United States Patent
Thiele

(10) Patent No.: US 10,052,076 B2
(45) Date of Patent: Aug. 21, 2018

(54) DIAGNOSTIC BRAIN IMAGING

(75) Inventor: Frank Olaf Thiele, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 941 days.

(21) Appl. No.: 14/112,045

(22) PCT Filed: Apr. 20, 2012

(86) PCT No.: PCT/IB2012/051990
§ 371 (c)(1),
(2), (4) Date: Oct. 16, 2013

(87) PCT Pub. No.: WO2012/147016
PCT Pub. Date: Nov. 1, 2012

(65) Prior Publication Data
US 2014/0031681 A1    Jan. 30, 2014

Related U.S. Application Data

(60) Provisional application No. 61/478,953, filed on Apr. 26, 2011.

(51) Int. Cl.
| | |
|---|---|
| *A01B 1/00* | (2006.01) |
| *A61B 6/00* | (2006.01) |
| *G06T 7/33* | (2017.01) |
| *A61B 6/03* | (2006.01) |
| *G06T 7/00* | (2017.01) |

(52) U.S. Cl.
CPC ............. *A61B 6/501* (2013.01); *A61B 6/037* (2013.01); *A61B 6/481* (2013.01); *A61B 6/5217* (2013.01); *G06T 7/001* (2013.01); *G06T 7/33* (2017.01); *A61B 6/508* (2013.01); *G06T 2207/10104* (2013.01); *G06T 2207/10108* (2013.01); *G06T 2207/30016* (2013.01)

(58) Field of Classification Search
None
See application file for complete search history.

(56) References Cited

U.S. PATENT DOCUMENTS

| | | |
|---|---|---|
| 6,821,504 B2 | 11/2004 | Wisniewski |
| 7,158,692 B2 | 1/2007 | Chalana |
| 7,873,405 B2 | 1/2011 | Burbar |
| (Continued) | | |

*Primary Examiner* — Katherine Fernandez
*Assistant Examiner* — Marjan Saboktakin

(57) ABSTRACT

A radiological imaging apparatus (10) acquires a radiological brain image of a subject after administration of a radio tracer binding to a target substance indicative of a clinical pathology. In one embodiment, the clinical pathology is amyloid deposits in the brain at a level correlative with Alzheimer's disease and the target substance is amyloid deposits. A processor (C) tests for the clinical pathology by: performing non-rigid registration of the brain image with a positive template (32P) indicative of having the clinical pathology and with a negative template (32N) indicative of not having the clinical pathology; generating positive and negative result metrics (36P, 36N) quantifying closeness of the registration with the positive and negative template respectively; and generating a test result (54) based on the positive result metric and the negative result metric. An independent test result is generated by quantifying a second mode of an intensity histogram for the brain image.

17 Claims, 3 Drawing Sheets

(56) References Cited

U.S. PATENT DOCUMENTS

Figure 1:
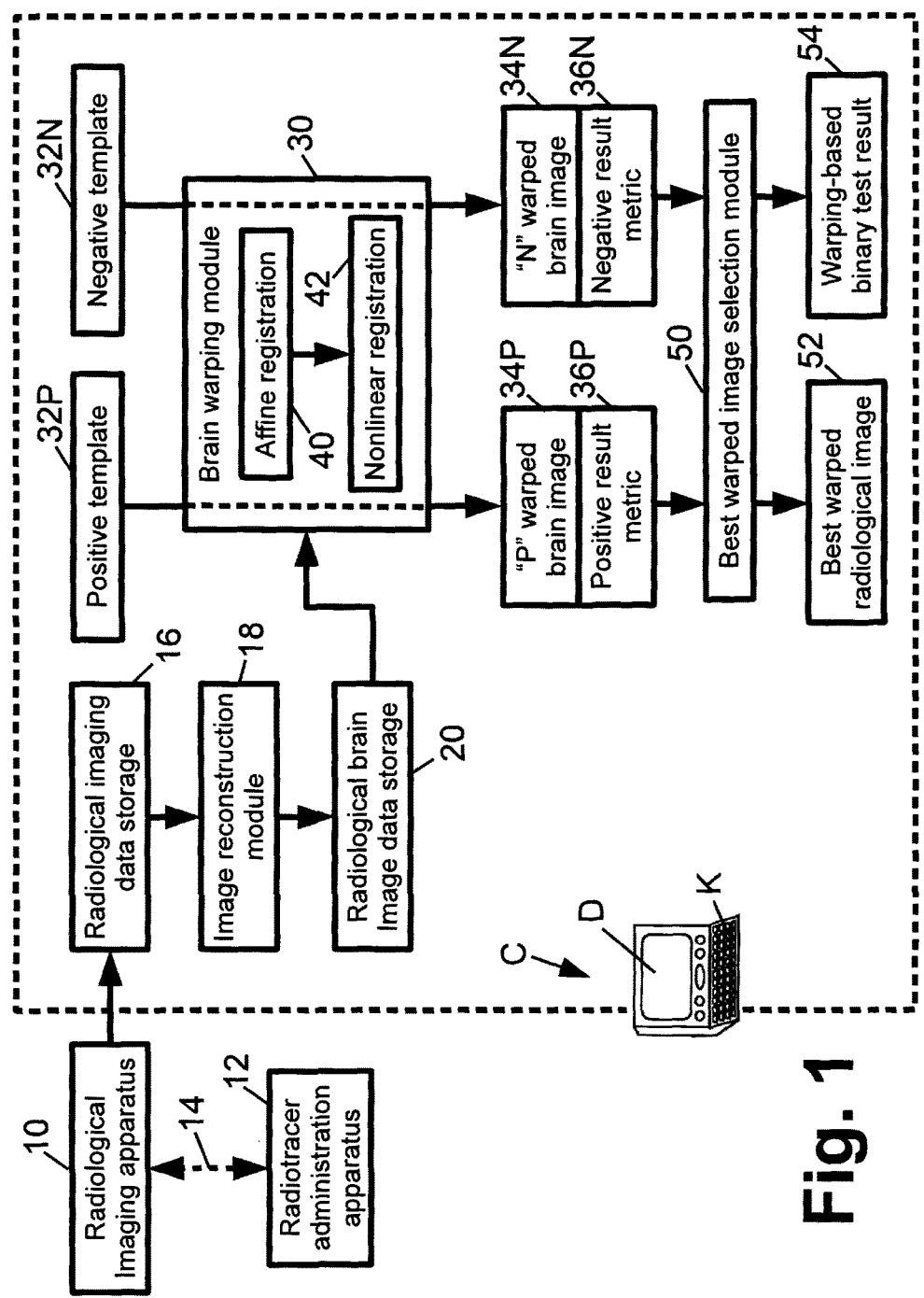

| | | | |
|---|---|---|---|
| 2005/0251014 A1* | 11/2005 | Qian | A61B 6/00 600/407 |
| 2005/0273007 A1 | 12/2005 | Burbar | |
| 2009/0290765 A1 | 11/2009 | Ishii | |
| 2010/0080432 A1 | 4/2010 | Lilja | |
| 2010/0145194 A1 | 6/2010 | Joshi | |
| 2010/0152577 A1 | 6/2010 | Young | |
| 2010/0331676 A1 | 12/2010 | Carpenter | |

* cited by examiner

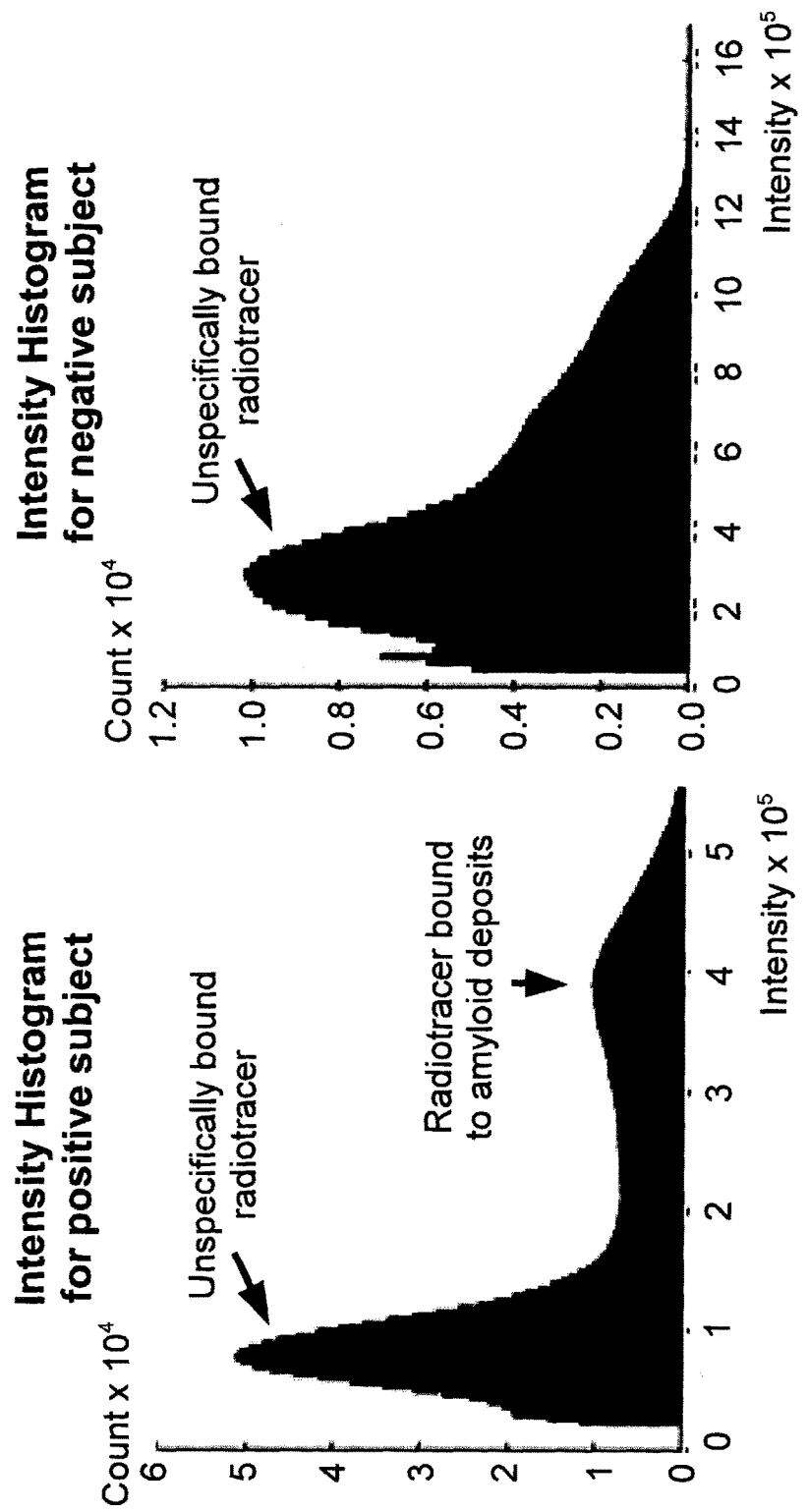

DIAGNOSTIC BRAIN IMAGING

CROSS REFERENCE TO RELATED APPLICATIONS

This application is a national filing of PCT application Serial No. PCT/IB2012/051990, filed Apr. 20, 2012, published as WO 2012/147016 A1 on Nov. 1, 2012, which claims the benefit of U.S. provisional application Ser. No. 61/478,953 filed Apr. 26, 2011, which is incorporated herein by reference.

The following relates to the medical diagnostic arts, radiological imaging arts, and related arts.

Alzheimer's disease and other types of dementia are debilitating conditions affecting millions. Early detection of the onset of such conditions can facilitate early intervention and improve patient health, quality of life, and overall outcome. In this regard, clinical studies have correlated enhanced amyloid deposition (Aβ) in brain tissue with the onset of Alzheimer's disease. The correlation between amyloid deposits and a clinical diagnosis of Alzheimer's disease is not one-to-one, and additional medical tests and expert medical examination are required to make a clinical diagnosis of Alzheimer's disease. However, the presence of substantial amyloid deposits in the brain is considered to be a hallmark of Alzheimer's disease pathology.

Advantageously, amyloid deposition can be detected non-invasively in vivo by performing radiological brain imaging in conjunction with certain radiotracers that bind to amyloid deposits in the brain. This makes such imaging a suitable tool for screening for Alzheimer's disease, and/or for providing probative information for diagnosing Alzheimer's disease in a patient (in conjunction with other medical tests, the results of expert medical examination, or so forth). In the case of positron emission tomography (PET) imaging, some suitable radiotracers available for research include [11C]-PIB, [18F]-Flutemetamol, [18F]-Florbetaben, and [18F]-Florbetapir. The three [18F]-labeled tracers are in clinical phase, and are expected to be approved by the Food and Drug Administration (FDA) for use in the United States in the near future. Single photon emission computed tomography (SPECT) is another radiological imaging technique that can be used to detect amyloid deposition in the brain. A promising SPECT amyloid radiotracer is IMPY (e.g., [123I]IMPY or [125I]IMPY), which has been used in research for several years.

While visual assessment of such images can be clinically useful, such visual assessment can be ambiguous. Quantitative assessment provides a better basis for clinical decisions, and in some jurisdictions may be mandatory for regulatory approval of the test for use in clinical diagnosis.

In general, several methods have been applied to quantify amyloid images. The gold standard in quantification is kinetic modeling of dynamic PET time series with arterial blood sampling to assess the concentration of radiotracer in the blood. However, arterial blood sampling is highly invasive and is preferably avoided. Acquisition of a dynamic time series of radiological images also requires that the patient remain in the imaging apparatus (preferably motionless) for an extended time period, which can be difficult for the patient.

In a more clinically compatible approach, ratios of standard uptake values (SUV) of static images are used for clinical assessment. The static image is suitably obtained about 30-40 min after injection of the radiotracer, and is acquired over an acquisition period of about 20 min. An SUV ratio (also denoted herein as SUVR) is obtained by dividing the mean SUV in a target region by the mean SUV in a reference region. For amyloid imaging the reference region is typically the cerebellar grey matter, which is believed to represent unspecific binding of the radioligands.

Each region of interest (ROI) in the PET image is delineated manually or by automatic segmentation. Manual delineation is time-consuming and introduces substantial variability and consequently low reproducibility. Automatic segmentation may be performed by image processing in the native image space based on image intensity and general tissue/region priors. Automatic segmentation may also be performed by warping of the PET image to a brain template (also sometimes referred to as a brain atlas). The template may be based on an anatomical image of the same subject generated by magnetic resonance (MR) imaging, or may be based on a radioligand-specific template. The use of an anatomical MR image as the template has the disadvantage of requiring the patient to undergo two imaging sessions: (1) MR imaging and (2) radiological imaging of an administered radiotracer. In contrast, the use of a radiotracer-specific template reduces the amount of imaging performed on the patient and expedites the performance of the diagnostic test.

Imaging of amyloid deposits for the screening and/or diagnosis of Alzheimer's disease or other dementia conditions is described herein as an illustrative application. More generally, however, the disclosed analyses are generally applicable to clinical assessment of a radiological brain image of a subject acquired after administration of a radiotracer to the subject that binds to a substance probative of a clinical condition.

The following provides new and improved apparatuses and methods as disclosed herein.

In accordance with one disclosed aspect, a method comprises: performing non-rigid registration of a radiological brain image of a subject acquired after administration of a radiotracer to the subject that binds to a target substance indicative of a clinical pathology with a positive template indicative of having the clinical pathology; performing non-rigid registration of the radiological brain image with a negative template indicative of not having the clinical pathology; generating a positive result metric quantifying closeness of the non-rigid registration of the radiological brain image with the positive template; and generating a negative result metric quantifying closeness of the non-rigid registration of the radiological brain image with the negative template. The method may further comprise generating a test result for the subject respective to the clinical pathology based on the positive result metric and the negative result metric. In some embodiments the clinical pathology is amyloid deposits in the brain at a level correlative with Alzheimer's disease and the target substance is amyloid deposits in the brain.

In accordance with another disclosed aspect, a method comprises: acquiring a radiological brain image of a subject after administration of a radiotracer to the subject that binds to a clinically probative substance; independently performing first and second tests on the acquired radiological brain image to generate respective first and second test results comprising first and second assessments of the presence of the clinically probative substance in the brain of the subject; and outputting the first and second test results in a human perceptible format. In some embodiments the second independently performed test comprises a constructing an intensity histogram for the radiological brain image and generating the second test result based on the histogram and the first test does not utilize said intensity histogram. In some embodiments the first independently performed test comprises performing non rigid registration of the radiological brain image with each of a plurality of different templates indicative of different respective levels of the clinically probative substance in the brain and generating the first test result based on the non rigidly registered images and the second test does not utilize said non rigidly registered images.

In accordance with another disclosed aspect, an apparatus comprises a digital processor configured to perform a method as set forth in either one of, or both of, the two immediately preceding paragraphs. In accordance with another disclosed aspect, a storage medium stores instructions that when executed by a digital processor perform a method as set forth in either one of, or both of, the two immediately preceding paragraphs.

In accordance with another disclosed aspect, an apparatus comprises a radiological imaging apparatus and a processor configured to perform a diagnostic test on a radiological brain image of a subject acquired by the radiological imaging apparatus after administration of a radiotracer to the subject that binds to amyloid deposits in the brain. The diagnostic test performed by the processor comprises: performing non-rigid registration of the radiological brain image with a positive template indicative of testing positive for amyloid deposits in the brain; performing non-rigid registration of the radiological brain image with a negative template indicative of testing negative for amyloid deposits in the brain; generating a positive result metric quantifying closeness of the registration of the clinical radiological brain image with the positive template; generating a negative result metric quantifying closeness of the registration of the clinical radiological brain image with the negative template; and generating a diagnostic test result based on the positive result metric and the negative result metric.

One advantage resides in more reliable clinical assessment of pathologies of interest by radiological imaging in conjunction with administration of a radiotracer.

Another advantage resides in more reliable assessment of amyloid deposit pathology (that has been correlated with Alzheimer's disease in clinical studies) by radiological brain imaging (e.g., using PET or SPECT) in conjunction with administration of a radiotracer that binds to amyloid deposits in the brain.

Another advantage resides in providing an improved Alzheimer's disease test that quantifies amyloid deposits in the brain, for use in conjunction with other data in diagnosing Alzheimer's disease in patients.

Another advantage resides in providing plural independent approaches for quantifying radiological brain imaging (e.g., using PET or SPECT) of an administered radiotracer that binds to amyloid deposits in the brain. The plural independent quantification approaches provide a consistency check on the test result.

Another advantage resides in more reliable detection and quantification of amyloid deposits (which are a hallmark of Alzheimer's disease) by radiological brain imaging (e.g., using PET or SPECT) in conjunction with administration of a radiotracer that binds to amyloid deposits in the brain, which is not dependent upon the use of a brain template or brain warp image processing.

Further advantages will be apparent to those of ordinary skill in the art upon reading and understanding the following detailed description.

FIG. 1 diagrammatically shows a system for performing a quantitative test for amyloid deposits in the brain by performing brain warp image processing on a brain image acquired by a radiological imaging apparatus in conjunction with an administered radiotracer that binds to amyloid deposits in the brain.

Figure 2:
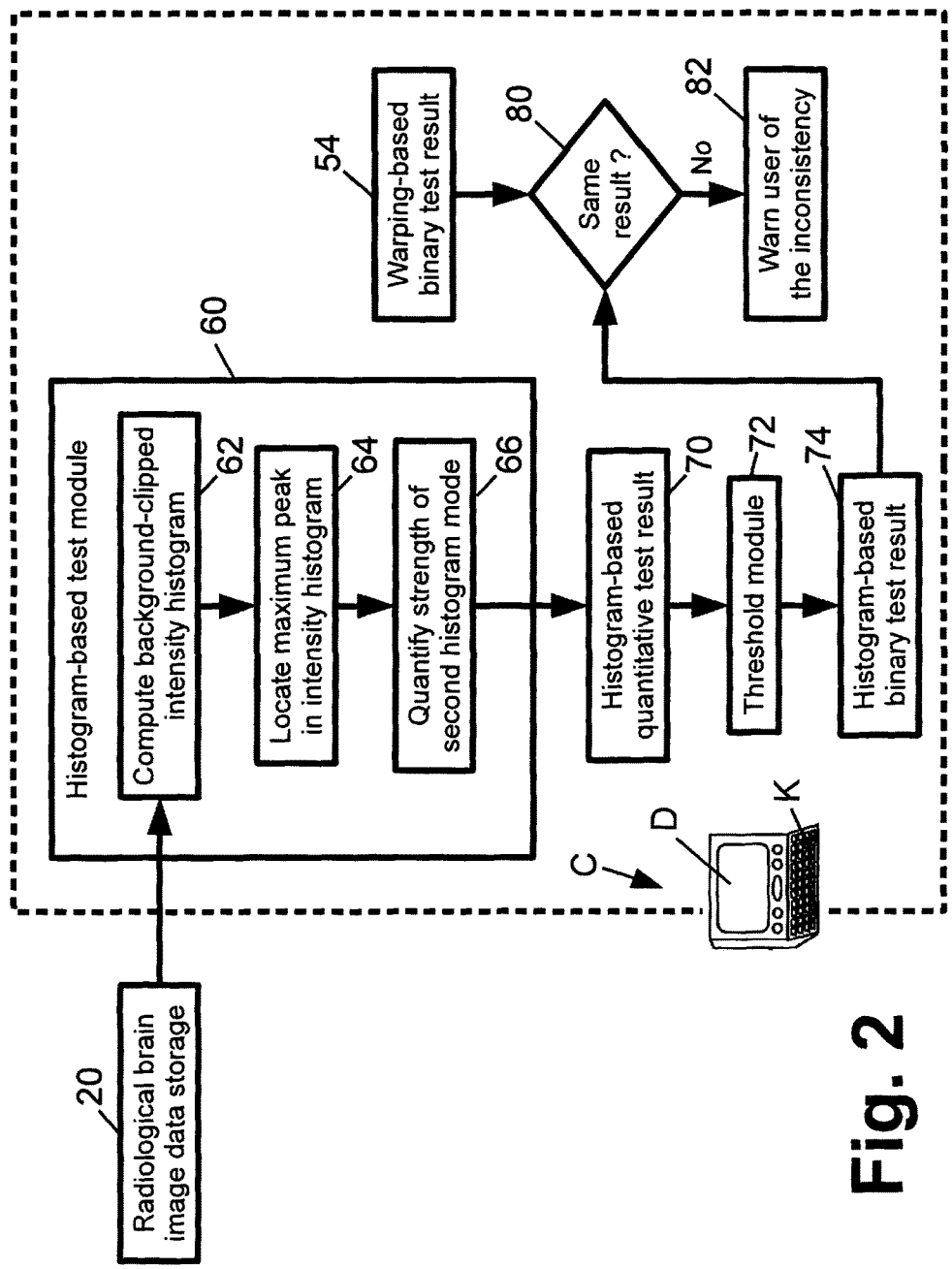

FIG. 2 diagrammatically shows a subsystem for performing a histogram-based quantitative test for amyloid deposits on the brain image, wherein the histogram-based image processing is independent of the brain warp image processing depicted in FIG. 1. Also shown in FIG. 2 is a consistency check comparing the results of the brain warp image processing and the histogram-based image processing.

FIGS. 3 and 4 diagrammatically show intensity histograms generated by the histogram-based test of FIG. 2 for a subject that tests positive for amyloid deposits (FIG. 3) and for a subject that tests negative for amyloid deposits (FIG. 4).

Disclosed herein are diagnostic analyses that are generally applicable to diagnostic analysis of a radiological brain image of a patient (or, more generally, of a subject, which term as used herein encompasses a human patient or other human subject, an animal veterinary subject, or so forth) acquired after administration of a radiotracer to the patient that binds to a substance probative of a clinical condition. Some diagnostic analyses disclosed herein are based on the recognition that existing brain warping approaches using a radiotracer-specific template fail to take into account a substantial variability in the appearance of radiological brain image for different pathologies. For example, consider the illustrative case of radiological brain imaging for detecting and quantifying amyloid deposition pathology correlating with Alzheimer's disease using a radiotracer binding to amyloid deposits. The brain of a patient having Alzheimer's disease generally has a high concentration of amyloid deposits in certain areas of the brain, leading to a radiological brain image having substantial "bright" content corresponding to radiotracer bound to amyloid deposits. In contrast, the brain of a patient who does not have Alzheimer's disease generally has a substantially lower concentration of amyloid deposits in the brain, leading to a radiological brain image having relatively low "bright" content. The radiotracer specific template may therefore fail to provide a reasonable correlation with the radiological brain image acquired for a given patient undergoing Alzheimer's disease screening or diagnosis.

Some brain image analyses disclosed herein are further based on the insight that, rather than being a problematic complication for the brain warping analysis, this high degree of variability can instead be incorporated into the brain warping analysis to provide diagnostic information without reliance upon SUVR or other post-warping analyses (although such post-warping analyses may also be performed).

With reference to FIG. 1, a radiological imaging apparatus 10 provides an image of a radiotracer that is administered to a patient using a radiotracer administration apparatus 12. By way of illustrative example, the radiological imaging apparatus 10 may be a PET or SPECT imaging apparatus (which optionally may be a multimodality imaging apparatus that also includes an additional imaging modality such as transmission computed tomography, or CT). By way of illustrative example, the radiotracer administration apparatus 12 may comprise an intravenous injection system for delivering the radiotracer directly into the patient's bloodstream. Alternatively, it is also contemplated for the radiotracer administration apparatus 12 to deliver the radiotracer to the patient via another pathway, such as orally by the patient consuming a liquid containing the radiotracer.

There is an operative communication pathway 14 between the radiological imaging apparatus 10 and the radiotracer administration apparatus 12 that ensures the radiological imaging apparatus 10 performs the radiological imaging at a suitable time after the radiotracer administration apparatus 12 delivers the radiotracer to the patient. The communication pathway 14 can be a purely manual pathway in which a human radiologist waits a predetermined time interval after administering the radiotracer before initiating the radiological brain imaging, or can be an automated pathway in which (by way of illustrative example) the radiological imaging apparatus 10 monitors counts of radiation detection events until the counts exceed a trigger threshold at which time the radiological brain imaging commences (optionally after a set delay period). This latter approach uses the radiological imaging apparatus 10 to detect when the radiotracer has accumulated in the brain at a level sufficient to perform the radiological brain imaging. The radiological brain imaging performed by the radiological imaging apparatus 10 can employ substantially any imaging technique, and can acquire a single radiological image or a time series of radiological images. While hereinafter a single radiological brain image is assumed, the disclosed processing can be repeated for each image of a time series, or the time series can be analyzed in a preprocessing step to select the radiological brain image having the highest brightness for processing (or another selection criterion can be employed).

The resulting radiological brain image is processed by a digital processing device, such as an illustrative computer C (e.g., a desktop computer, notebook computer, tablet computer, remote server, dedicated imaging apparatus controller, or so forth) to perform the disclosed clinical diagnostic processing. The digital processing device C includes radiological imaging data storage 16 for storing the acquired radiological imaging data. The acquired imaging data may take various forms depending upon the type of radiological imaging apparatus 10. In the case of a PET imaging apparatus, each imaging datum suitably comprises a "line of response", or LOR, connecting two simultaneously occurring 511 keV gamma particle detection events (corresponding to a single positron-electron annihilation event). In some embodiments, the PET imaging apparatus has sufficient time resolution to distinguish any small time difference between the two "simultaneous" 511 keV gamma particle detection events, and this "time-of-flight" or TOF information is used to localize the positron-electron annihilation along the LOR. An example of such a TOF-PET system is the Ingenuity™ TF PET/CT (a multimodality imaging apparatus available from Koninklijke Philips Electronics N.V., Eindhoven, The Netherlands, that provides both TOF-PET and transmission CT imaging modalities). In the case of a SPECT imaging apparatus, the imaging data may be suitably formatted as list-mode imaging data in which each imaging datum corresponds to a linear or small-angle conical localization of a particle emission event.

An image reconstruction module 18 implemented by the digital processing device C performs image reconstruction on the acquired radiological imaging data to generate a radiological brain image that is suitably stored in a radiological brain image data storage 20. The image reconstruction module 18 employs a suitable image reconstruction algorithm such as iterative backprojection, filtered backprojection, or so forth, to reconstruct the acquired imaging data to form the reconstructed radiological brain image.

With continuing reference to FIG. 1, a brain warping module 30 registers the acquired radiological brain image of the subject to a brain template. To alleviate the problem of substantial variability in the appearance of radiological brain image for different pathologies, and to even further take advantage of such variability in the brain warp processing to perform clinical diagnosis, the brain warping module 30 registers the acquired radiological brain image to two or more brain templates including at least one positive template 32P and at least one negative template 32N. The positive template 32P is representative of images for persons testing positive for the clinically probative pathology (e.g., testing positive for amyloid deposits in the brain at quantities shown to have correlation with Alzheimer's disease), and may by way of illustrative example be generated by averaging the radiological brain images of a pool of reference subjects who have tested positive for amyloid deposits in the brain. Similarly, the negative template 32N is representative of not testing positive for amyloid deposits in the brain, and may by way of illustrative example be generated by averaging the radiological brain images of a pool of reference subjects who have tested negative for amyloid deposits in the brain. The registration by the brain warping module 30 of the radiological brain image of the subject to the positive template 32P generates a "P" warped radiological brain image 34P and a corresponding positive result metric 36P quantifying closeness of the registration of the radiological brain image with the positive template 32P. Similarly, the registration by the brain warping module 30 of the radiological brain image of the subject to the negative template 32N generates a "N" warped radiological brain image 34N and a corresponding negative result metric 36N quantifying closeness of the registration of the radiological brain image with the negative template 32N.

The brain warping module 30 can employ substantially any type of non-rigid image registration process to perform the brain warping. The illustrative brain warping module 30 performs a two-step registration process: an affine registration 40 followed by a nonlinear registration 42 using the output of the affine registration 40 as a starting point. In some suitable embodiments, the nonlinear registration 42 employs a B-spline nonlinear registration algorithm. Optionally, the nonlinear registration 42 includes a regularization to penalize strong deformation. The result metrics 36P, 36N can employ various cost functions for quantifying the closeness of the registration. For the illustrative brain warping module 30, the result metrics 36P, 36N may be computed as the cost function of the affine registration 40 only, or as the cost function of the nonlinear registration 42 only, or as a combination of both. Some suitable cost functions include cross-correlation, (normalized) mutual information, or so forth.

With continuing reference to FIG. 1, a best warped image selection module 50 compares the positive and negative result metrics 36P, 36N to identify a best warped image 52 and a corresponding warping-based binary test result 54. For example, if the result metrics 36P, 36N are cost functions and the positive result metric 36P indicates a lower registration cost as compared with the negative result metric 36N, then the selection module 50 selects the "P" warped radiological brain image 34P as the best warped image 52, and selects the corresponding "positive" test result as the warping-based binary test result 54. On the other hand, if the negative result metric 36N indicates a lower registration cost as compared with the positive result metric 36P, then the selection module 50 selects the "N" warped radiological brain image 34N as the best warped image 52, and selects the corresponding "negative" test result as the warping-based binary test result 54.

The warping-based binary test result 54 is referred to herein as an Alzheimer's disease test result, because the test result 54 is probative of whether or not the patient has Alzheimer's disease. However, it is to be understood that the test result 54 is actually a metric or indicator of amyloid deposits in the brain, and is not, by itself, sufficient to make a diagnosis of Alzheimer's disease. Rather, a diagnosis of Alzheimer's disease is made based on the test result 54 in conjunction with other probative information (e.g., other medical tests probative of Alzheimer's disease, results of a physical examination of the patient by qualified medical personnel, or so forth). As another application, the test result 54 may be used as a screening test, such that a patient for which the test result 54 is positive will then undergo additional clinical tests, physical examination, or other clinical evaluation in order to make an ultimate diagnosis.

Although not illustrated, a non-binary warping-based test result can additionally or alternatively be generated, for example based on the difference between (or ratio of) the positive and negative result metrics 36P, 36N. Thus, if the positive result metric 36P is a very low cost value and the negative result metric 36N is a very high cost value, then the non-binary warping-based test result would be a quantitative value indicating a strong positive result. On the other hand, if the positive result metric 36P is a cost value that is only slightly lower than the value of the negative result metric 36N, then the non-binary warping-based test result would be a quantitative value indicating a less strong (or weak) positive result. The non-binary warping-based test result can be a distinct result, or can be applied as a confidence measure for the binary test result 54.

In the embodiment of FIG. 1, two templates 36P, 36N are used, with one template 36P being indicative of having the clinical condition (e.g., having Alzheimer's disease) and the other template 36N being indicative of not having the clinical condition (e.g., not having Alzheimer's disease).

It will be appreciated that warping to both positive and negative templates 32P, 32N and then selecting the best result has substantial advantages. It reduces the likelihood of obtaining poor registration to the template due to the substantial variability in the appearance of radiological brain image for different pathologies. Even further, it affirmatively uses this variability in the brain warp processing stage to generate the clinical result 54. It will be noted that this clinical result 54 is obtained without computing SUV ratios or other quantitative assessments of the (best) warped radiological brain image 52. Optionally, SUVR or other values are computed from the (best) warped radiological brain image 52. In such a case, the clinical result 54 serves as a consistency or verification check for the SUVR result (which is treated as the "true" result).

In the embodiment of FIG. 1, registration to two different templates 36P, 36N is performed, with one template 36P being indicative of testing positive for amyloid deposits (at a level clinically significant for Alzheimer's disease evaluation) and the other template 36N being indicative of testing negative for amyloid deposits. However, if the variability in the appearance of radiological brain image for different pathologies is too great, then using only two templates may result in both templates providing relatively poor registration. In such cases, a third template (or even a fourth, or more, templates) may be added.

In some embodiments, the third template is an intermediate template that is indicative of a state intermediate between the amyloid deposit-positive condition and the amyloid deposit-negative condition. The intermediate template is suitably derived from reference subjects for whom the concentration of amyloid deposits is intermediate (that is, higher than is statistically typical for patients believed to not have Alzheimer's disease and lower than is statistically typical for patients believed to have Alzheimer's disease). The brain warping to the intermediate template produces a corresponding intermediate result metric that is also taken into account by the selection module 50 in generating the test result 54. In some embodiments, if the intermediate result metric is larger than both the positive result metric 36P and the negative result metric 36N then the test result 54 is "indefinite" or the like.

In some embodiments, the third template is a second positive template. In other words, in these embodiments two (or more) different positive templates are provided, both (or all) of which are representative of images acquired of persons who have tested positive for amyloid deposits in the brain. The use of two (or more) positive templates enables the brain warping to accommodate substantial patient-to-patient variability in the appearance of the radiological brain image within the category of patients who have tested positive for amyloid deposits in the brain. The selection module 50 suitably takes into account the positive result metric generated for each of the two (or more) positive templates in generating the test result 54. In similar fashion, two or more negative templates can also be provided—however, since the negative result corresponds to low brightness content in the radiological brain image, the amount of patient-to-patient variability amongst patients testing negative for amyloid deposits in the brain is generally lower than the variability amongst patients testing positive for amyloid deposits in the brain.

As already mentioned, the disclosed brain warping approach using positive and negative templates 32P, 32N is obtained without computing SUV ratios or other quantitative assessments of the (best) warped radiological brain image 52. As also already mentioned, SUVR or other values are optionally computed from the (best) warped radiological brain image 52. However, it will be noted that these SUVR values may have some bias due to the use of the best brain image 52, which is warped to match a particular (e.g., positive or negative) template.

With reference to FIG. 2, in some embodiments a verification check is performed using a wholly independent image processing that does not utilize any results of the brain warping processing. In the illustrative example of FIG. 2, the independent image processing comprises a histogram-based clinical test performed by a histogram-based test module 60. This test operates on the reconstructed radiological brain image without warping (e.g., recalled from the radiological brain image data storage 20 and without processing by the brain warping module 30). An intensity histogram is constructed by the test module 60 in an operation 62. To reduce noise, the operation 62 optionally clips or omits from the histogram low-intensity "background" values having intensity below a background threshold. In some embodiments, the background threshold is 25% of the image mean intensity. In some embodiments, the background threshold is 10% of the maximum intensity in the image. Optionally, the operation 62 smoothes or otherwise processes the histogram to remove noise and/or outliers or other statistical anomalies.

With continuing reference to FIG. 2 and with brief reference to FIGS. 3 and 4, the histogram-based clinical test is based on the following observations. The radiotracer is chosen to bind to a target substance indicative of a clinical condition. In the illustrative example, the clinical condition is the presence of amyloid deposits (which, again, is a hallmark of Alzheimer's disease), and the target substance is amyloid deposits in the brain. However, not all of the radiotracer binds to the target substance. Rather, a substantial portion, or even the majority, of the radiotracer remains as unspecifically bound radiotracer causing a background signal throughout substantial portions or all of the brain tissue. As seen in FIG. 3, this results in a dual-mode histogram. A first mode occurs at relatively low intensity and corresponds to the background signal produced by the unspecifically bound radiotracer. Assuming that the amount of target substance in the brain is relatively low, as is expected to be the case for amyloid deposits correlative with Alzheimer's disease, it follows that most of the radiotracer will actually be in the unspecifically bound state so that the first mode has a corresponding peak that is the largest peak in the histogram. However, since the first mode corresponds to a background signal, that largest peak occurs at relatively low intensity (that is, a low value on the histogram x-axis which corresponds to intensity).

A second mode corresponds to the radiotracer bound to the target substance (e.g., bound to amyloid deposits in the illustrative case). This mode will be weaker than the first mode since the low concentration of the target substance (e.g., amyloid deposits) in the brain means that a low fraction of the total radiotracer in the brain will be bound to the target substance. But, since the radio tracer is designed to bind to the target substance, this low fraction of the total radiotracer is highly concentrated in the low volume of the target substance. As a consequence the second mode has a lower peak at higher intensity as compared with the first mode. This second mode peak is labeled as "Radiotracer bound to amyloid deposits" in FIG. 3.

With particular reference to FIG. 4, the comparison of an intensity histogram for a negative subject (that is, a subject who does not have amyloid deposits in the brain, in the illustrative case) is shown. In this case there will be no second mode (or, a negligible second mode) for the reason that there is little or no amount of the target substance (e.g., amyloid deposits) in the brain. As a consequence, as seen in FIG. 4 the histogram is substantially single-mode with a single peak at low intensity corresponding to the unspecifically bound radiotracer generating the background signal.

With returning reference to FIG. 2, in view of the foregoing the histogram-based test module 60 performs the following processing on the (optionally smoothed, optionally low-intensity-clipped) histogram generated by the operation 62. In an operation 64, the largest peak in the histogram is identified. As just discussed, this largest peak is expected to correspond to the first mode, that is, to the background signal generated by unspecifically bound radiotracer. Then, in an operation 66, the strength of the second mode is quantified. This quantification value is used, either directly or after further processing such as normalization or the like, as a histogram-based quantitative test result 70. This reflects the foregoing discussion showing that the second mode corresponds to radiotracer bound to the target substance, so that the strength of the second mode is a suitable metric of the amount of target substance in the brain. By way of some illustrative examples, the quantification 66 can compute a position of the second-largest peak corresponding to the second mode, a ratio of number of voxels in the high intensity range (or, more generally, belonging to the second mode) versus the number of voxels in the low intensity range (or, more generally, belonging to the first mode), or so forth. The "membership" of voxels in the first or second mode can be assessed in various ways, such as based on ranges defined by mean or median/quantile of clipped histogram and FWHM as measured in the histogram itself or based on pre-defined values, or based on peak fitting assuming the first and second modes have a particular (e.g., Gaussian or Lorentzian) shape.

In another illustrative example of the quantification 66, the intensity scale of the radiological brain image may be normalized such that the intensity corresponding to the largest peak of the intensity histogram (that is, the peak of the first or background mode) has a pre-defined value, and computing the histogram-based test result by quantifying a distribution of voxels of the normalized brain image having intensity higher than the pre-defined value (and hence having intensity above the background level and likely corresponding to radiotracer bound to the target substance). More generally, the largest (first) maximum in the intensity histogram can be used to perform intensity normalization of the image, normalizing the intensity at the maximum to a pre-defined value. This value can be adjusted to correspond to the standard normalization to the cerebellar grey matter. Since the intensity at the histogram maximum does not represent a typical grey matter value, the calibration to cerebellar grey matter may also include other statistical properties of the histogram, e.g. FWHM or intensity maximum.

With continuing reference to FIG. 2, the histogram-based quantitative test result 70 is optionally thresholded by a threshold module 72 to generate a histogram-based binary test result 74. The threshold employed by the threshold module 72 is selected such that: (1) if the test result 70 is higher than the threshold then the histogram-based binary test result 74 is positive, indicating the patient tests positive for (a clinically significant level of) amyloid deposits in the brain; and (2) if the test result 70 is lower than the threshold then the histogram-based binary test result 74 is negative, indicating the patient tests negative for amyloid deposits in the brain. The threshold is suitably chosen when configuring the histogram-based test by computing the test result 70 for a pool of reference subjects, some of whom have tested amyloid deposit-positive and some of whom have tested amyloid deposit-negative. The threshold to be employed by the threshold module 72 is chosen to most accurately discriminate whether a reference subject has amyloid deposits at a level clinically significant for assessment of Alzheimer's disease, or not, based on the reference subject's test result.

With continuing reference to FIG. 2, the histogram-based binary test result 74 is generated without any contribution from the processing performed by the brain warping module 30, and conversely the warping-based binary test result 54 is generated without any contribution from the processing performed by the histogram-based test module 60. It follows that the two binary test results 54, 74 can serve as a validation check on one another. Toward this end, FIG. 2 diagrammatically shows a validation check module 80 that compares the two binary test results 54, 74. If the results are not the same (e.g., if the warping-based binary test result 54 is amyloid deposit-positive while the histogram-based binary test result 74 is amyloid deposit-negative, or vice versa) then the validation check module 80 suitably outputs a warning 82 in human-perceptible form (for example, as a warning message displayed on a display device D of the digital processing device C) informing the radiologist of the inconsistency.

More generally, various outputs can be displayed in human-perceptible form, such as: the best warped radiological brain image 52; the histogram generated by the operation 62; one or both binary test results 54, 74; quantitative results (e.g., test result 70) shown either as separate results or as confidence metrics applied to the corresponding binary test result; the aforementioned inconsistency warning 82 if output by the validation check module 80; and so forth.

The digital processing device C suitably implements the various storage components 16, 20 as a magnetic disk or other magnetic medium, an electronic memory such as random access memory (RAM) or flash memory, an optical storage medium, various combinations thereof, or so forth. The digital processing device C suitably implements the various processing modules 18, 30, 50, 60, 72, 80 by executing suitable software and/or firmware instructions, wherein the software and/or firmware are suitably stored on a storage medium (not shown) such as a magnetic disk or other magnetic medium, an electronic memory such as random access memory (RAM) or flash memory, an optical storage medium, various combinations thereof, or so forth. Optionally, the digital processing device C may also include an illustrative keyboard K or other user input device via which the radiologist or other user can configure the radiological brain scan acquisition, set various parameters for the processing, or otherwise interact with the imaging apparatus 10 and/or processing components 18, 30, 50, 60, 72, 80.

The illustrative example set forth herein relates to clinical screening or assessment of Alzheimer's disease based on quantitative analysis of amyloid deposits in the brain as detected by radiological imaging of a radiotracer that binds to the amyloid deposits. More generally, however, the disclosed clinical diagnostic approaches are suitably employed for substantially any clinical diagnosis operating on a radiological brain image of a subject acquired after administration of a radiotracer to the subject that binds to a target substance indicative of a clinical condition. In such applications there will generally be substantial variability in the appearance of radiological brain image for different pathologies due to substantial differences in the amount and/or distribution of the target substance in the brain. (If there are no substantial differences, then the target substance is unlikely to be probative of the underlying clinical condition). Accordingly, the disclosed approach of brain warping to positive and negative templates and making a diagnosis based on the best registration is expected to be generally useful for clinical diagnosis of radiological brain images obtained in conjunction administering a radiotracer binding to a probative target substance.

Moreover, in a living subject the target substance will generally be a small fraction of the total brain tissue, and so the dual-mode histogram described with reference to FIGS. 3 and 4 for the specific case of amyloid deposits, and the related histogram-based test described with reference to FIG. 2, are expected to also be generally useful for clinical diagnosis of radiological brain images obtained in conjunction administering a radiotracer binding to a probative target substance.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A method comprising:
    performing non-rigid registration of a radiological brain image of a subject acquired after administration of a radiotracer to the subject that binds to a target substance indicative of a clinical pathology with a positive template indicative of having the clinical pathology wherein the non-rigid registration with the positive template employs a cost function quantifying the closeness of the non-rigid registration and generates a positive result metric comprising the value of the cost function output by the non-rigid registration of the radiological brain image with the positive template;
    performing non-rigid registration of the radiological brain image with a negative template indicative of not having the clinical pathology wherein the non-rigid registration with the negative template employs the cost function quantifying the closeness of the non-rigid registration and generates a negative result metric comprising the value of the cost function output by the non-rigid registration of the radiological brain image with the negative template;
    generating a test result for the subject respective to the clinical pathology based on the positive result metric generated by the non-rigid registration of the radiological brain image with the positive template and the negative result metric generated by the non-rigid registration of the radiological brain image with the negative template, wherein the generated test result indicates the presence or absence of the clinical pathology of the brain; and
    displaying the test result on a display device;
    wherein the non-rigid registration operations and the generating operation are performed by a digital processing device.

2. The method of claim 1, wherein the generating of a test result comprises generating one of:
    a positive test result if the positive result metric and the negative result metric indicate relatively better registration of the radiological brain image with the positive template than with the negative template, and
    a negative test result if the positive result metric and the negative result metric indicate relatively better registration of the radiological brain image with the negative template than with the positive template.

3. The method of claim 1, further comprising:
    performing non-rigid registration of the radiological brain image with an intermediate template indicative of a state intermediate between having the clinical pathology and not having the clinical pathology; and
    generating an intermediate result metric quantifying closeness of the registration of the radiological brain image with the intermediate template;
    the generating of the test result for the subject respective to the clinical pathology being further based on the intermediate result metric.

4. The method of claim 1, wherein:
    the non-rigid registration of the radiological brain image with the positive template comprises performing non-rigid registration of the radiological brain image with two or more different positive templates each indicative of having the clinical pathology;
    the generating of a positive result metric comprises generating a positive result metric for each positive template that quantifies closeness of registration of the radiological brain image with that positive template; and
    the generating of a test result is based on the plural positive result metrics and the negative result metric.

5. The method of claim 1, further comprising:
    constructing an intensity histogram for the radiological brain image;

identifying a largest peak of the intensity histogram, the largest peak corresponding to a first histogram mode; and computing a histogram-based test result by quantifying a second histogram mode different from the first histogram mode.

6. The method of claim 5, wherein the computing comprises:

computing the histogram-based test result by quantifying one of (i) the intensity at which a second-largest peak of the intensity histogram occurs and (ii) a ratio of the number of voxels of the radiological brain image belonging to the first histogram mode and the number of voxels of the radiological brain image belonging to the second histogram mode.

7. The method of claim 5, further comprising:

thresholding the histogram-based test result to generate a binary histogram-based test result selected from a group consisting of a positive histogram-based test result corresponding to a relatively stronger second histogram mode and a negative histogram-based test result corresponding to a relatively weaker second histogram mode.

8. The method of claim 5, further comprising:

determining whether the test result and the histogram-based test result are consistent; and outputting a human-perceptible warning if the test result and the histogram-based test result are not consistent.

9. The method of claim 1, further comprising:

computing a warping based confidence test result, which is different from the test result, using the radiological brain image non-rigidly registered to the positive or negative template selected by the test result; and determining whether the warping based confidence test result is consistent with the test result.

10. The method of claim 1, wherein:

the clinical pathology is amyloid deposits in the brain at a level correlative with Alzheimer's disease, and the target substance is amyloid deposits in the brain.

11. The method of claim 1, further comprising:

administering the radiotracer to the subject; and subsequent to the administering, acquiring the radiological brain image by using positron emission tomography (PET) performed by a PET imaging apparatus or single photon emission computed tomography (SPECT) imaging performed by a SPECT imaging apparatus.

12. An apparatus configured to perform a method as set forth in claim 1, the apparatus including the digital processing device programmed to perform the non-rigid registration operations and the generating operation and the display for displaying the test result.

13. An apparatus comprising:

a radiological imaging apparatus;

a processor configured to perform a diagnostic test on a radiological brain image of a subject acquired by the radiological imaging apparatus after administration of a radiotracer to the subject that binds to amyloid deposits in the brain, the diagnostic test comprising:

performing non-rigid registration of the radiological brain image with a positive template indicative of testing positive for amyloid deposits in the brain and generating a positive result metric quantifying closeness of the registration of the clinical radiological brain image with the positive template wherein the positive result metric comprises a value of a cost function output by the non-rigid registration of the clinical radiological brain image with the positive template;

performing non-rigid registration of the radiological brain image with a negative template indicative of testing negative for amyloid deposits in the brain and generating a negative result metric quantifying closeness of the registration of the clinical radiological brain image with the negative template wherein the negative result metric comprises a value of the cost function output by the non-rigid registration of the clinical radiological brain image with the negative template; and generating a diagnostic test result based on the positive result metric output by the non-rigid registration of the clinical radiological brain image with the positive template and the negative result metric output by the non-rigid registration of the clinical radiological brain image with the negative template wherein the generated diagnostic test result indicates the presence or absence of amyloid deposits in the brain; and A display device configured to display the generated diagnostic test result.

14. The apparatus of claim 13, wherein the processor is further configured to perform a histogram-based diagnostic test comprising:

constructing an intensity histogram for the radiological brain image;

identifying a largest peak of the intensity histogram, the largest peak corresponding to a first histogram mode; and computing a histogram-based diagnostic test result by quantifying a second histogram mode different from the first histogram mode.

15. The apparatus of claim 14, wherein the processor is further configured to generate a warning indication if the diagnostic test result and the histogram-based diagnostic test result are not consistent.

16. The apparatus of claim 13, wherein the generating of a diagnostic test result based on the positive result metric and the negative result metric comprises generating one of:

a positive test result if the positive result metric and the negative result metric indicate relatively better registration of the radiological brain image with the positive template than with the negative template, and a negative test result if the positive result metric and the negative result metric indicate relatively better registration of the radiological brain image with the negative template than with the positive template.

17. A non-transitory storage medium storing instructions that when executed by a digital processing device perform a method comprising:

performing non-rigid registration of a radiological brain image of a subject acquired after administration of a radiotracer to the subject that binds to amyloid deposits in the brain with a positive template indicative of having amyloid deposits in the brain at a level correlative with Alzheimer's disease and generating a positive result metric quantifying closeness of the registration of the radiological brain image with the positive template wherein the positive result metric comprises a value of a cost function output by the non-rigid registration of the radiological brain image with the positive template;

performing non-rigid registration of the radiological brain image with a negative template indicative of not having amyloid deposits in the brain at a level correlative with Alzheimer's disease and generating a negative result metric quantifying closeness of the registration of the radiological brain image with the negative template wherein the negative result metric comprises a value of the cost function output by the non-rigid registration of the radiological brain image with the negative template;

generating a test result for the subject respective to whether the subject has amyloid deposits in the brain at a level correlative with Alzheimer's disease based on the positive result metric output by the non-rigid registration of the radiological brain image with the positive template and the negative result metric output by the non-rigid registration of the radiological brain image with the negative template including displaying the test result on a display device, wherein the generating of a test result comprises generating one of:

a positive test result if the positive result metric and the negative result metric indicate relatively better registration of the radiological brain image with the positive template than with the negative template, and a negative test result if the positive result metric and the negative result metric indicate relatively better registration of the radiological brain image with the negative template than with the positive template.

* * * * *